United States Patent [19]

Nakamura et al.

[11] Patent Number: 4,957,936
[45] Date of Patent: Sep. 18, 1990

[54] GLYCOCYAMIDINE DERIVATIVES

[75] Inventors: Ko Nakamura; Kazuharu Ienaga, both of Hyogo, Japan

[73] Assignee: Nippon Zoki Pharmaceutical Co., Ltd., Osaka, Japan

[21] Appl. No.: 472,494

[22] Filed: Jan. 30, 1990

[30] Foreign Application Priority Data

Feb. 1, 1989 [JP] Japan .................................. 1-24669

[51] Int. Cl.$^5$ .................. C07D 233/88; A61K 31/415
[52] U.S. Cl. ..................................... 514/389; 548/308
[58] Field of Search ......................... 548/308; 514/389

Primary Examiner—Alan L. Rotman
Assistant Examiner—Joseph K. McKane
Attorney, Agent, or Firm—Armstrong, Nikaido, Marmelstein, Kubovcik & Murray

[57] ABSTRACT

The glycocyamidine derivatives of the present invention are represented by the following formula (I):

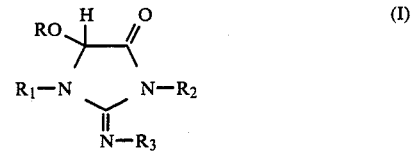

wherein $R_1$, $R_2$ and $R_3$, which may be the same or different, is hydrogen or a lower alkyl group, preferably a straight or branched alkyl group having 1 to 3 carbon atoms, such as methyl, ethyl, propyl or isopropyl, and R represents hydrogen or an acetyl group.

which are useful as test reagents for diagnosis of renal failure.

4 Claims, No Drawings

GLYCOCYAMIDINE DERIVATIVES

BACKGROUND OF THE INVENTION

The present invention relates to novel glycocyamidine derivatives and salts thereof which are useful as test reagents for diagnosis of renal failure.

In renal failure such as uremia, chronic nephritis or urinary obstruction, lowering of glomerular filtration rate caused by functional decrease of kidney is observed. The test measuring glomerular filtration rate is usually used to diagnose the renal failure. In particular, the creatinine clearance test based on blood and urinal creatinine level is often used.

As a result of investigations for metabolism of creatinine and the like in renal failure, the inventors of the present invention isolated and identified a novel compound from urine of patients suffering from renal failure. It was observed that this compound was increasingly produced and accumulated in the body at the diseased state such as renal failure. Therefore, it can be easy to make a diagnosis of various renal failures based on the existence and the amount of the compound in the fluid such as serum or cerebrospinal fluid and the urine.

SUMMARY OF THE INVENTION

An object of the present invention is to provide novel glycocyamidine derivatives which are useful as test reagents for diagnosis of renal failure.

DETAILED DESCRIPTION OF THE INVENTION

The glycocyamidine derivatives of the present invention are represented by the following formula (I).

$$\text{(I)}$$

In the above formula (I), $R_1$, $R_2$ and $R_3$, which may be the same or different, is hydrogen or a lower alkyl group, preferably a straight or branched alkyl group having 1 to 3 carbon atoms, such as methyl, ethyl, propyl or isopropyl. R represents hydrogen or an acetyl group.

The compounds of the above formula (I) can be represented by the following formula (II) or (III) as tautomeric isomers.

$$\text{(II)} \quad \text{(III)}$$

wherein each of $R_1$, $R_2$, $R_3$ and R has the same meaning as in the formula (I).

The glycocyamidine derivatives of the present invention include pharmaceutically acceptable salts of the compounds having above formula (I), for example, salts with alkali metal such as sodium or potassium, with alkaline-earth metal such as magnesium, calcium or barium, or with other metals such as aluminum, or salts as acid addition with an acid such as hydrochloric acid, sulfuric acid, nitric acid, phosphoric acid, formic acid, acetic acid, citric acid or lactic acid, or salts with an organic base such as ammonia or the like. These salts can be prepared from free glycocyamidine derivatives or other salts of these derivatives by a known method.

When optional isomers exist in the compounds of the invention, the present invention includes any of the DL-, D- and L-isomers.

The glycocyamidine derivatives of the present invention can be prepared as follows.

For example, the compounds represented by the following formula (IV) can be used as starting materials.

$$\text{(IV)}$$

wherein each of $R_1$, $R_2$ and $R_3$ has the same meaning as in the formula (I).

The 1-position, 3-position and/or an amino group of 2-position of the compound of the formula (IV) are protected by a conventional amino-protecting group such as t-butoxycarbonyl group, and then an acetoxy group is introduced into the 5-position of the compound by treatment with an oxidizing agent such as lead tetraacetate. The amino-protecting group is removed by a conventional method, for example, t-butoxycarbonyl group is removed by using trifluoroacetic acid, and then the acetoxy group is reduced in usual way to give 5-hydroxyglycocyamidine derivatives.

The resulting compounds of the present invention can be purified by known methods such as distillation chromatography and recrystallization. Identification is established through melting point (m.p.), elemental analysis, IR, NMR, UV, mass spectrum, etc.

EXAMPLE

The following examples, which are illustrative only and not intended to limit the scope of the invention, describe the preparation of the compounds of the present invention.

EXAMPLE 1

(1) 10 g of 1-methylglycocyamidine and 29 g of t-butoxycarbonyl anhydride were dissolved in 300 ml of dimethylformamide, and stirred overnight at 60° C. The solution was concentrated to dryness and 100 ml of water was added to the residue. The resulting product was extracted by 100 ml of acetic acid twice. The organic layer was concentrated to dryness under reduced pressure. The residue was purified by silica gel column chromatography (70% ethylacetate/hexane) to give 12.6 g of $N^2$-t-butoxycarbonyl-1-methylglycocyamidine in the form of pale yellow needle crystals.

m.p.: 109–110 ° C.

In the same manner, the following compounds were obtained.

$N^2$-t-butoxycarbonyl-3-methylglycocyamidine
3-t-butoxycarbonyl-$N^2$-methylglycocyamidine
1,$N^2$-di-t-butoxycarbonylglycocyamidine (2) 11.6 g of N²-t-butoxycarbonyl-1methylglycocyamidine and 36.2 g of lead tetraacetate were dissolved in 300 ml of dried benzene. The solution was refluxed with heating for 90 minutes and then cooled to room temperature. A small amount of water was added thereto. After removing the resulting precipitate and aqueous layer, the organic layer was dried over sodium sulfate anhydride. The resulting solution passed through a short column of silica gel and concentrated under reduced pressure to give 5-acetyl-N2-t-butoxycarbonyl-1-methylglycocyamidine as an oily substance. Without any further purifications, this oily residue was used in the following reaction.

In the same manner, the following compounds were obtained.

5-acetyl-N²-t-butoxycarbonyl-3-methylglycocyamidine
5-acetyl-3-t-butoxycarbonyl-N²-methylglycocyamidine
5-acetyl-1,N²-di-t-butoxycarbonylglycocyamidine (3) 100 ml of trifluoroacetic acid was added to the resulting products as mentioned above. The solution was stirred for an hour at room temperature to remove the protecting group to give 5-acetyl 1-methylglycocyamidine, which was used in the following reaction without any further purifications.

In the same manner, the following compounds were obtained.

5-acetyl-3-methylglycocyamidine
5-acetyl-N²-methylglycocyamidine
5-acetylglycocyamidine (4) The solvent was distilled off under reduced pressure. 100 ml of 1N hydrochloric acid was added to the residue and the reaction mixture was stirred for 2 days at room temperature. The solution was concentrated to dryness. The crude crystals were washed with ethyl acetate and recrystallized from ethanol to give 8.1 g of 5-hydroxy-1-methylglycocyamidine hydrochloride (Compound 1).

m.p.: 191 ° C. (decomposition)

Elementary Analysis: $C_4H_8N_3O_2Cl$

|  | C % | H % | N % |
|---|---|---|---|
| Calculated | 29.02 | 4.87 | 25.38 |
| Found | 29.10 | 4.82 | 25.70 |

MS (EI, 70eV): 129 (M+), 127, 101, 73, 56, 42
NMR(DMSO-$d_6$/TMS): $\delta$=3.01(3H,s), 5.13(1H,d,J=6Hz), 7.69(1H,d,J=6Hz), 9.28(1H,s), 9.42(1H,s)

In the same manner, the following compounds were obtained.

5-hydroxy-3-methylglycocyamidine hydrochloride (Compound 2)

m.p.: 186 ° C. (decomposition)
NMR(DMSO-$d_6$/TMS): $\delta$=3.07(3H,s), 5.35(1H,d,J=9Hz), 7.43(1H,d,J=9Hz), 7.83(1H,br.s), 8.47(1H,br.s), 8.54(1H,br.s)

5-hydroxy-N²-methylglycocyamidine hydrochloride (Compound 3)

m.p.: 172 ° C. (decomposition)
NMR(DMSO-$d_6$/TMS): $\delta$=2.92(3H,s), 5.30+5.36(1H,s), 7.39+7.54(1H,br.s), 9.54+9.65(1H,br.s), 9.97+10.50(1H,br.s), 12.48(1H,br.s)

5-hydroxyglycocyamidine hydrochloride (Compound 4)

m.p.: 220 ° C. (decomposition)
NMR(DMSO-$d_6$/TMS): $\delta$=4.82(1H,d,J=7.8Hz), 6.21(1H,d,J=7.8Hz), 7.07(1H,br.s), 7.64(1H,br.s), 7.83(1H,br.s)

It was observed that the compound 1 of the present invention was increasingly produced and accumulated in the body in patients suffering from renal failure. It is very important for evaluating the diseased state to determine the compound 1 in the fluid such as serum or cerebrospinal fluid and the urine, particularly, the determination of the existence and the amount change of the compound in serum of renal failure patients is very useful for diagnosis of renal failure, and so that provides an easy diagnosis method. Therefore, the compounds of the present invention are useful as test reagents for diagnosis of renal failure such as uremia, chronic nephritis or urinary obstruction.

What is claimed is:

1. A glycocyamidine derivative having the formula (I) or a pharmaceutically acceptable salt thereof:

$$\underset{\underset{N-R_3}{\parallel}}{RO\underset{R_1-N\quad N-R_2}{\overset{H\quad O}{\diagdown\diagup}}}\quad (I)$$

wherein $R_1$, $R_2$ and $R_3$, which may be the same or different, is hydrogen or a lower alkyl group, and R is hydrogen or an acetyl group.

2. A glycocyamidine derivative according to claim 1 wherein $R_1$ is a lower alkyl group.

3. A glycocyamidine derivative according to claim 2 wherein $R_2$, $R_3$ and R is hydrogen.

4. A glycocyamidine derivative according to claim 3 wherein $R_1$ is methyl group.

* * * * *